(12) United States Patent
Chen (10) Patent No.: US 12,286,392 B2
(45) Date of Patent: Apr. 29, 2025

(54) SYSTEMS AND METHODS FOR PRODUCING ULTRA-LOW CARBON INTENSITY ETHANOL

(71) Applicant: Cellulosic Ethanol Technologies, LLC, Galva, IA (US)

(72) Inventor: Ye-Mon Chen, Galva, IA (US)

(73) Assignee: CELLULOSIC ETHANOL TECHNOLOGIES, LLC, Galva, IA (US)

( * ) Notice: Subject to any disclaimer, the term of this patent is extended or adjusted under 35 U.S.C. 154(b) by 330 days.

(21) Appl. No.: 17/933,992

(22) Filed: Sep. 21, 2022

(65) Prior Publication Data
US 2023/0093071 A1   Mar. 23, 2023

Related U.S. Application Data

(60) Provisional application No. 63/246,848, filed on Sep. 22, 2021.

(51) Int. Cl.
*C07C 29/80* (2006.01)
*C07C 29/00* (2006.01)

(52) U.S. Cl.
CPC .............. *C07C 29/80* (2013.01); *C07C 29/00* (2013.01)

(58) Field of Classification Search
CPC ................................................. C07C 29/74–84
See application file for complete search history.

(56) References Cited

U.S. PATENT DOCUMENTS

2020/0171404 A1 * 6/2020 Lucas .................... B01D 53/02

* cited by examiner

*Primary Examiner* — Medhanit W Bahta
(74) *Attorney, Agent, or Firm* — HOVEY WILLIAMS LLP (57) ABSTRACT

Processes and systems for producing cellulosic ethanol from byproducts of an ethanol production facility and methods and systems for more effectively integrating traditional ethanol production facilities with cellulosic ethanol production to reduce overall energy use and produce ethanol with lower carbon intensity scores.

8 Claims, 10 Drawing Sheets

SYSTEMS AND METHODS FOR PRODUCING ULTRA-LOW CARBON INTENSITY ETHANOL

CROSS REFERENCE TO RELATED APPLICATION

The current patent application is a nonprovisional application which claims priority benefit, with regard to all common subject matter, of earlier-filed U.S. Provisional Patent Application Ser. No. 63/246,848, titled "SYSTEMS AND METHODS FOR PRODUCING ULTRA-LOW CARBON INTENSITY ETHANOL", filed Sep. 22, 2021. The earlier-filed provisional patent application is hereby incorporated by reference, in its entirety, into the current patent application.

BACKGROUND

The production of ethanol for use as a gasoline additive or a straight liquid fuel continues to increase as petroleum costs rise and environmental concerns about fossil fuel's high carbon emissions become more pronounced. Conventional ethanol may be produced in a dry milling process by grinding corn or other grains into a powder or flour and then liquefying, fermenting, and distilling it to produce alcohol, carbon dioxide, and byproducts. Conventional ethanol production processes produce ethanol from the starch portion of the grain but do not produce additional ethanol from the fiber portions of the grain, which are primarily found in the byproducts. Instead, the byproducts are typically dehydrated and used as animal feed.

U.S. Pat. No. 8,633,003, the teachings of which are incorporated by reference into the present application in their entirety, discloses systems and methods for producing cellulosic ethanol from the fiber portions of grains, which, as mentioned above, are mostly unused byproducts of existing ethanol production facilities. Although such cellulosic ethanol production improves the environmental impact of ethanol by producing additional ethanol from byproducts, it unfortunately requires substantial amounts of energy. Reducing greenhouse gas (GHG) emissions is widely believed to be the most important way to minimize the adverse effects of climate change. The transportation sector is responsible for as much as 50% of GHG emissions. California has thus implemented Low Carbon Fuel Standards (LCFS) in an attempt to reduce the GHG emissions from the transportation sector. Other states and governments have implemented or are considering similar actions.

The LCFS assigns a carbon intensity (CI) score to all transportation fuels. CI is the measure of GHG emissions associated with producing, distributing, and consuming a fuel and is measured in grams of carbon dioxide equivalent per megajoule (gCO2e/MJ). A fuel with a lower CI score is better for the environment than a fuel with a relatively higher CI score.

Biofuels, such as conventional corn ethanol, can have relatively low CI scores because the $CO_2$ emitted from vehicles during biofuel combustion is considered carbon neutral, as the carbon released was previously uptaken from the atmosphere by the corn or other plant used to create the biofuel. But conventional corn ethanol production has GHG emissions resulting from the fertilizer used to grow the plants; the energy of tractors and other vehicles to plant, cultivate, harvest, and transport corn to the ethanol plants; and the ethanol production processes. Some ethanol plants have made significant progress in reducing GHG emissions and hence have improved the CI of conventional ethanol from ~99 in 1990 to as low as 50's and 60's for the top quartile ethanol plants in 2020, as shown in bars #1 and #2 in FIG. 5. This demonstrates that conventional corn ethanol can have lower CI scores than fossil fuel based gasoline, which has a CI of ~95.

Cellulosic ethanol has even lower CI scores. Because cellulosic ethanol is produced from corn residuals or other byproducts of an existing ethanol production facility, and because these byproducts, including the fibers, are classified as agriculture waste with zero CI, cellulosic ethanol production is not burdened by GHG emissions from planting, harvesting, and transporting grains. Thus, cellulosic ethanol has a much lower CI of 39, as shown in bar #3 in FIG. 5. However, as mentioned above, cellulosic ethanol production is energy intensive, thus limiting its ability to lower its CI levels further, as per prior art of U.S. Pat. No. 8,633,003.

SUMMARY

The present invention solves the above-described problems and provides a distinct advantage over the current state-of-art of ethanol production processes. More particularly, the present invention provides processes and systems for producing additional cellulosic ethanol from byproducts of an ethanol production facility and methods and systems for more effectively integrating traditional ethanol production facilities with cellulosic ethanol production facilities to reduce overall energy use and produce cellulosic ethanol with carbon intensity scores to as low as 23, as shown in bar #4 in FIG. 5; and by further combining this effective energy integration process and system for producing ethanol containing liquid products with the carbon capture and sequestration (CCS) process and system for sequestrating CO2 containing gas products from the facilities, the additional cellulosic ethanol produced from the facilities can achieve ultra-low CI of near zero, as shown in bar #7 in FIG. 5, exceeding the current benchmark of the lowest state-of-art of California EV with CI of 19.9, as shown in bar #8 in FIG. 5.

Objectives of the invention are to produce ethanol from both the starch and fiber components of grains in a manner that reduces overall energy use and that produces additional cellulosic ethanol with an extremely low CI score of near zero when combining with the CCS process and system for sequestrating the CO2 containing gas products from the facilities. The present invention achieves these objectives and others by more efficiently and effectively integrating and managing the energy use and transfer between a traditional ethanol production facility and a cellulosic ethanol production process.

An embodiment of the invention is a process for creating ethanol that broadly comprises creating a first supply of ethanol from starch components of grains with a first distillation device that requires energy of a first amount and an evaporator that requires energy of a second amount. The process further comprises creating a second supply of ethanol from fiber portions of the grains with a second distillation device that requires energy of a third amount. To integrate and manage energy use of the two ethanol production processes, the process comprises energy cascading steps, where waste energy and other energy is sequentially transferred from devices requiring the greatest heat or other energy to devices requiring lesser heat or energy so as to reuse some of the energy. In one particular embodiment, this energy cascading is achieved by transferring at least some of the energy from the second distillation device to the evaporator to reduce energy requirements of the evaporator and transferring at least some of energy from the evaporator to the first distillation device to reduce energy requirements of the first distillation device.

Another embodiment of the invention is a process for creating ethanol that comprises creating a first supply of ethanol from starch components of grains with a first distillation device. This step also creates heated whole stillage from fiber portions of the grains. The process further comprises passing the heated whole stillage from the first distillation device to a second distillation device, where the second distillation device creates a second supply of ethanol and pre-treated whole stillage. The pre-treated whole stillage is then passed to an evaporator for drying. To integrate the energy requirements of the two ethanol production steps, the process further comprises using energy in the heated whole stillage to provide at least some of the energy requirements of the second distillation device and using energy in the pre-treated whole stillage to provide at least some of the energy requirement of the evaporator.

Another embodiment of the invention is a process for producing additional ethanol with ultra-low carbon intensity comprising producing a first ethanol containing liquid product from a first fermenter, wherein the first fermenter converts fermentable sugars from the starch components of the grains to the first ethanol containing liquid product and a first $CO_2$ containing gas product. The first ethanol containing liquid product from the first fermenter is sent to a first distillation device that operates at a first temperature and requires energy of a first amount and an evaporator that operates at a second temperature and requires energy of a second amount, the second temperature being higher than the first temperature. The process further comprises producing a second additional ethanol containing liquid product from a second fermenter, wherein the second fermenter converts fermentable sugars from the fiber portions of the grains to the second ethanol containing liquid product and a second $CO_2$ containing gas product. The second ethanol containing liquid product from the second fermenter is sent to a second distillation device that operates at a third temperature and requires energy of a third amount, the third temperature being higher than the second temperature. The process further comprises transferring at least part of the third amount of energy from the second distillation device to the evaporator to reduce at least part of the second amount of energy requirements for the evaporator. The process further comprises transferring at least part of the second amount of energy from the evaporator to the first distillation device to reduce at least part of the first amount of energy requirements of for the first distillation device. The process further comprises collecting, processing, compressing, transporting, and injecting the first and the second $CO_2$ containing gas products into an underground storage site.

This summary is provided to introduce a selection of concepts in a simplified form that are further described in the detailed description below. This summary is not intended to identify key features or essential features of the claimed subject matter, nor is it intended to be used to limit the scope of the claimed subject matter. Other aspects and advantages of the present invention will be apparent from the following detailed description of the embodiments and the accompanying drawing figures.

BRIEF DESCRIPTION OF THE DRAWING FIGURES

Embodiments of the present invention are described in detail below with reference to the attached drawing figures, wherein.

The drawing figures do not limit the present invention to the specific embodiments disclosed and described herein. The drawings are not necessarily to scale, emphasis instead being placed upon clearly illustrating the principles of the invention.

DETAILED DESCRIPTION

Figure 1:
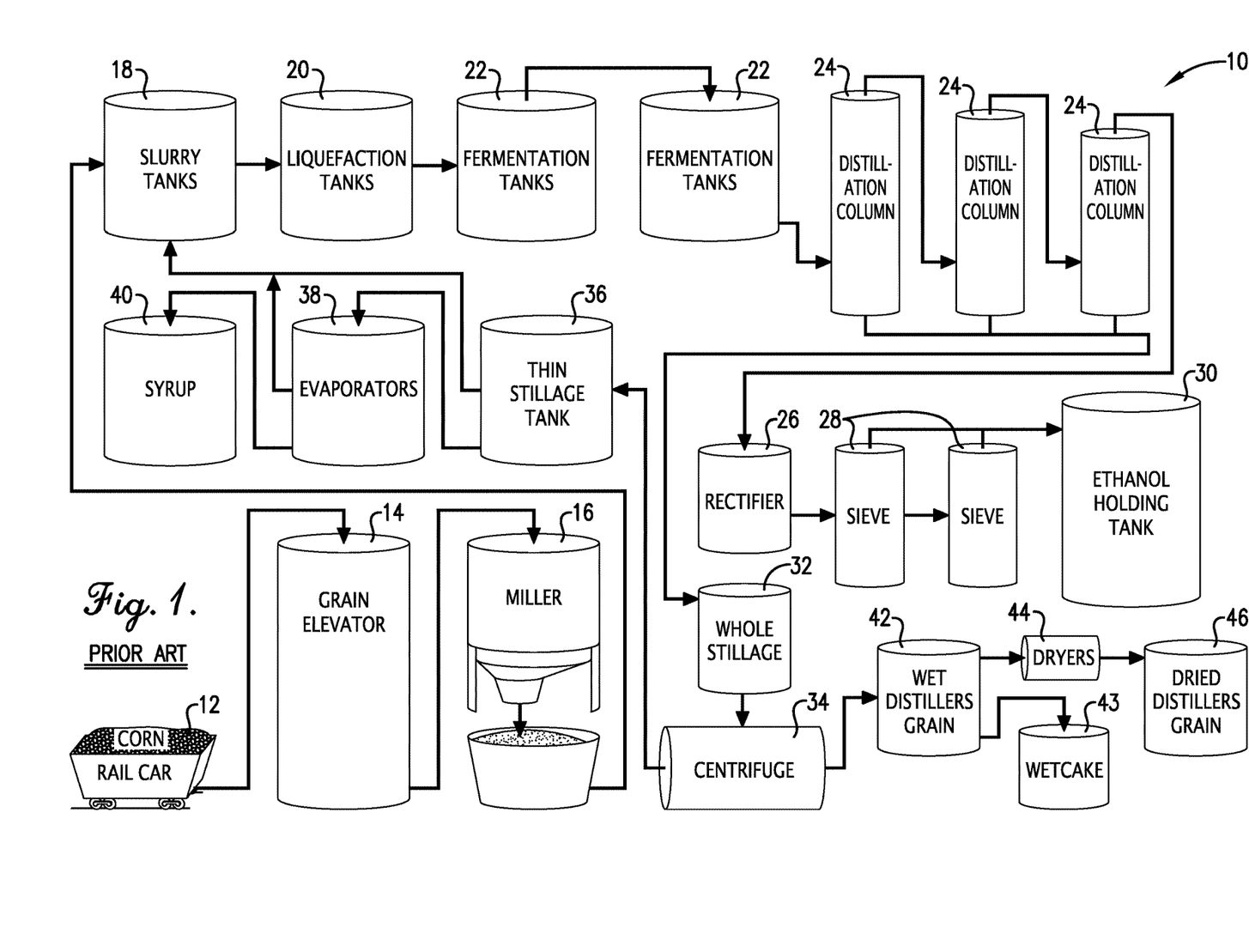
FIG. 1 is a schematic diagram of a prior art ethanol production facility.

FIG. 1 is a schematic illustration of the primary components of a conventional ethanol production facility 10. The facility 10 is shown for purposes of describing aspects of the present invention and can be replaced, in whole or part, by other ethanol production facilities or components without departing from the scope of the present invention. Other ethanol production facilities and processes are described and illustrated in U.S. Pat. Nos. 6,660,506 and 7,527,941 and U.S. Patent Application No. 2004/0023349, all of which are incorporated in their entireties into the present application by reference.

Returning to FIG. 1, grain 12, such as corn, is first delivered to the ethanol production facility 10 by railcars, trucks, or other means. The grain may also be barley, rye, wheat, oats, sorghum, milo, canola, or soybeans. A sufficient supply of the grain to operate the production facility may be stored in one or more grain elevators 14, bins, or other storage vessels.

Ethanol production begins by milling or otherwise processing the grain into a fine powder or flour by a hammer mill or other milling machine 16. The milled grain is then mixed with water and enzymes in one or more slurry tanks 18 and held in these tanks or liquefaction tanks 20 for a sufficient amount of time to enable the enzymes to begin to breakdown the starch in the mixture into fermentable sugars.

The mixture is then passed to one or more fermentation tanks 22 where yeast is added. The fermenting process creates a mixture that contains alcohol, solids, and liquids and that is commonly referred to as "beer.". FIG. 1 only shows the main process steps following the flow of the solid/liquid steam; however, the fermentation process also produces a CO2 containing gas, which is not shown in FIG. 1.

The beer is then transferred to one or more distillation columns 24, also often referred to as "beer strippers", which separate the alcohol from the solids and the liquids. The alcohol exits the top of these columns 24 and is transferred to one or more rectifiers 26 to remove moisture from the alcohol. The alcohol may also be passed to one or more molecular sieves 28 to remove even more moisture. The final alcohol is then transferred to one or more ethanol holding tanks 30 where it may be denatured before use as a fuel or fuel additive.

The liquid and solid mixture that remains in the distillation columns 24 after the alcohol has been removed is commonly referred to as "whole stillage" or simply "stillage". The whole stillage falls to the bottom of the distillation columns 24 and is then transferred to one or more whole stillage holding tanks 32. The whole stillage may then be passed through one or more centrifuges 34 which separate it into a stream of "thin stillage" and a stream of "wet distillers grain". The thin stillage is mostly liquid but may also contain a small amount of solid materials. The thin stillage may be held in one or more tanks and is typically returned to the slurry tanks 18 or some other part of the ethanol production facility 10 that requires water. Some or all of the thin stillage may also be transferred to one or more evaporators 38 to produce evaporated thin stillage, which is commonly referred to as "syrup". The syrup may be held in one or more tanks 40 and be used as an animal feed additive.

The wet distillers grain, which is often referred to as "wetcake", may be held in storage facilities 42, 43 and sold as a livestock feed. Some of the wet distillers grain may also be transferred to one or more dryers 44 to remove liquid therefrom to produce dried distillers grain, which may also be stored in one or more tanks 46 and used as livestock feed. In addition, some of the syrup can be dried with the wet distillers grains to produce dried distillers grains with solubles (DDGS).

The above described ethanol production facility 10 does not attempt to produce ethanol from the whole stillage removed from the distillation columns 24. Instead, the whole stillage is just a byproduct of the ethanol production process and is either used as livestock feed, make-up water, and/or is discarded. The processes of the present invention produce additional useable ethanol from the fiber portions of the whole stillage and any leftover starch after the main ethanol extraction is complete. The processes of the present invention also increase the protein content of the final byproducts, thus improving their nutrient value when used as livestock feed.

Since whole stillage is the byproduct of the fermentation of corn or other cereal grain, it contains a sizable fraction of fiber. All fiber is made up of hemicellulose, cellulose, and lignin. Lignin is a binder and is not fermentable into ethanol. Cellulose consists of glucose molecules, the same as in starch, but the linkages in cellulose make it more difficult to break down into individual glucose molecules than in starch. Hemicellulose contains a mixture of sugars and is generally easier to breakdown than cellulose. The processes of the present invention include steps for converting both the hemicellulose and cellulose portions of the whole stillage into sugars that may be fermented into ethanol.

Figure 2:
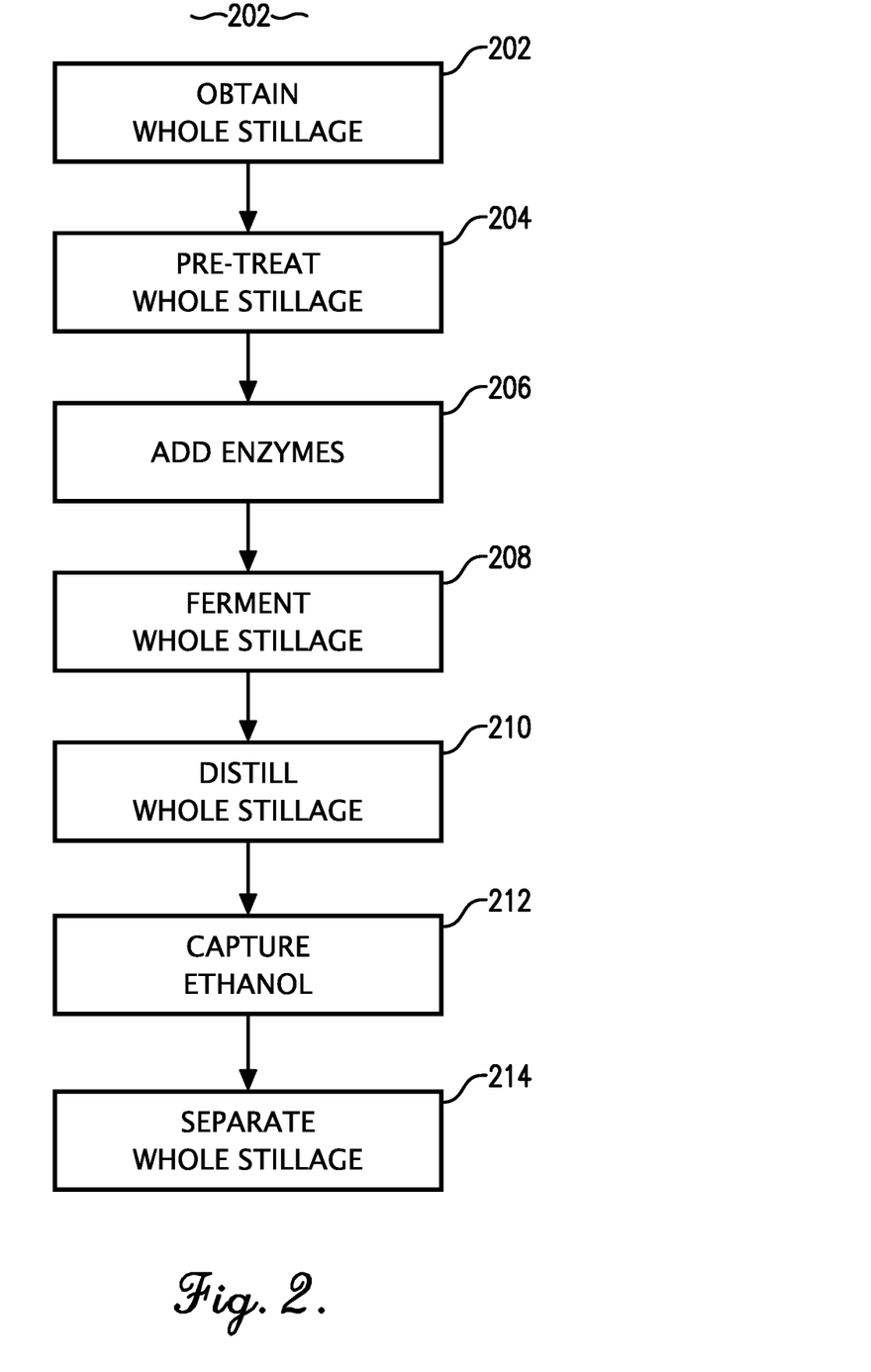
FIG. 2 is a flow diagram depicting a process of producing additional ethanol from byproducts of the ethanol production facility of FIG. 1.

The flow chart of FIG. 2 shows the steps in a process 200 for producing ethanol from whole stillage as disclosed in U.S. Pat. No. 8,633,003. The functions noted in the various blocks may occur out of the order depicted in FIG. 2. For example, two blocks shown in succession in FIG. 2 may in fact be performed substantially concurrently, or the blocks may sometimes be performed in the reverse order depending upon the functionality involved.

Figure 3:
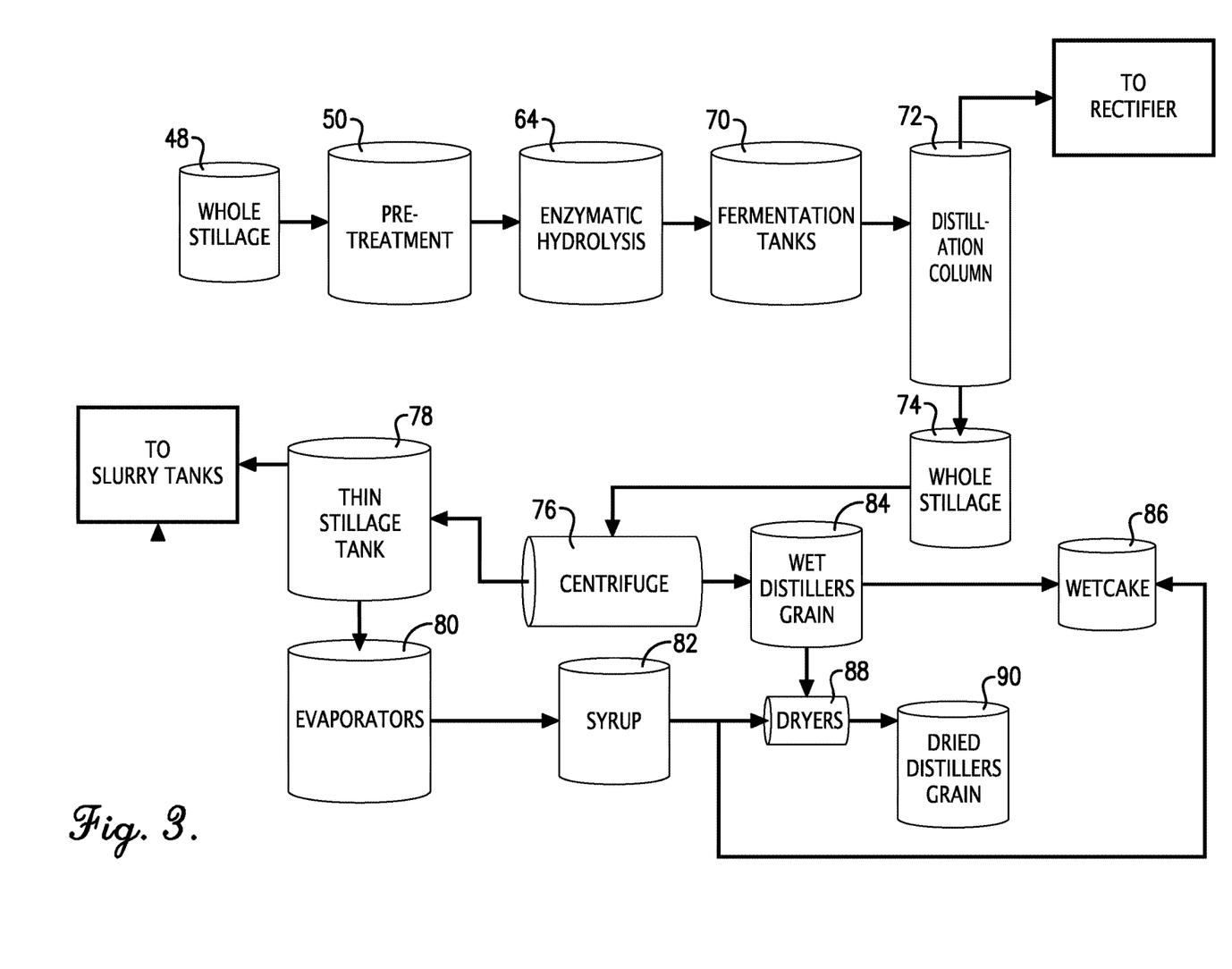
FIG. 3 is a schematic diagram of a system that may be used to implement the process of FIG. 2.
Figure 4:
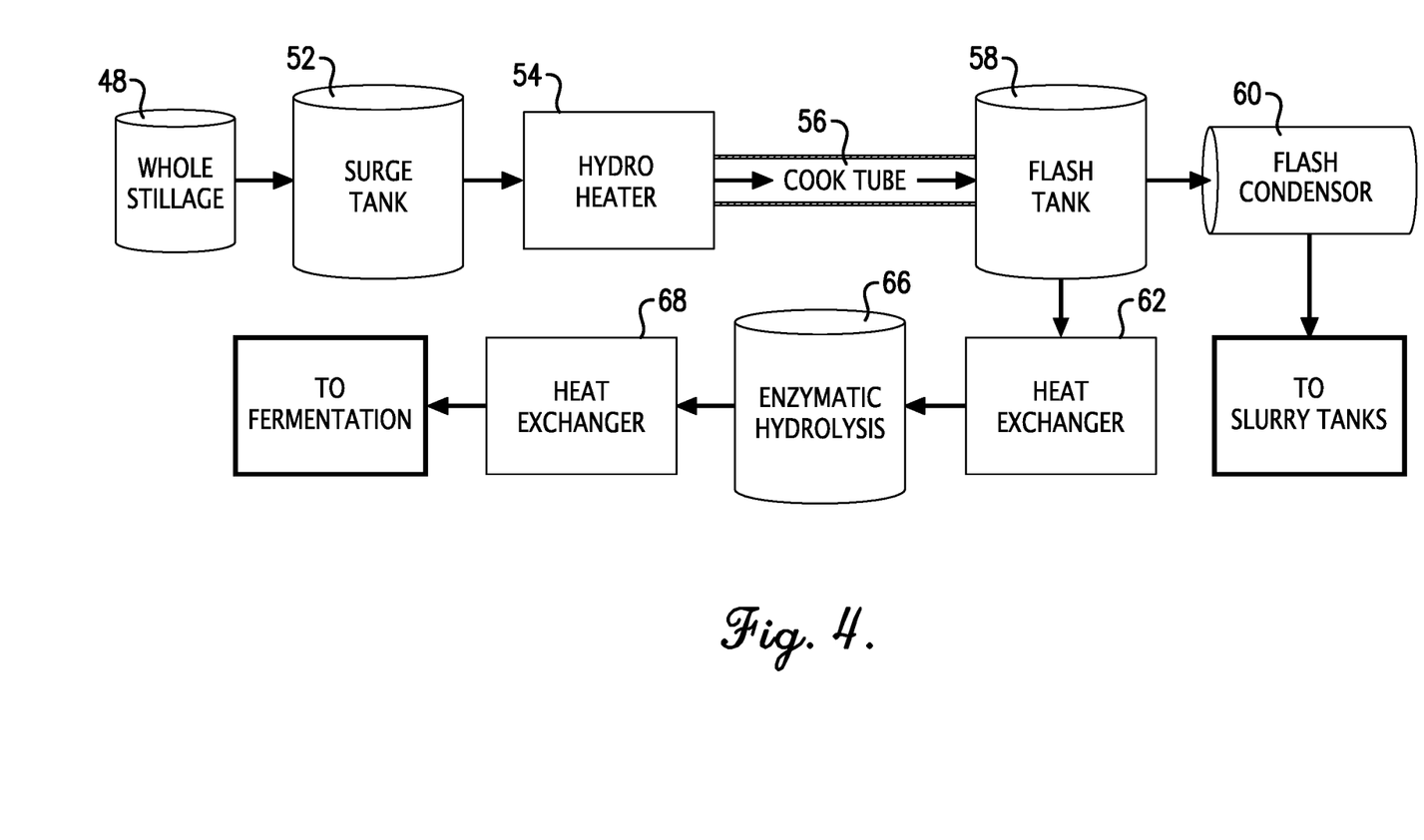
FIG. 4 is a schematic diagram depicting parts of the system of FIG. 3 in more detail.

Moreover, other embodiments of the process 200 may include additional steps not shown in FIG. 2 and/or may omit some of the steps shown in FIG. 2. The schematic diagrams of FIGS. 3 and 4 depict equipment that may be used to implement the process 200 and other embodiments of the process. The illustrated equipment may be replaced with other equipment without departing from the scope of the invention.

The process 200 starts by obtaining whole stillage as depicted in block 202. The whole stillage may be obtained from the distillation columns 24 or the whole stillage tanks 32 shown in FIG. 1 or elsewhere in the ethanol production facility 10 and may be held in one or more tanks 48 as depicted in FIG. 3. At this point in the process, the whole stillage has already been subjected to: 1) a long soak time in the liquefaction tanks 20 and fermenting tanks 22, 2) heating in the distillation steps, and 3) chemical reactions from the chemicals added throughout the ethanol production process. These steps help to facilitate the breakdown of the fiber in the whole stillage. The whole stillage is further treated in the process 200 of the present invention to continue the breakdown of the fiber for extracting additional ethanol.

The whole stillage may also be concentrated prior to further processing. One way of concentrating the fiber in the whole stillage is to employ a separation step prior to pretreatment and fermentation. This would entail processing a portion of the whole stillage through a machine such as press or a centrifuge to separate the supernatant (thin stillage) and the solids portion (wet distiller's grains) then reintroduce the wet distiller's grains into the unprocessed portion of the whole stillage. This has the tendency to reduce the volume of liquid thereby reducing chemical and energy costs, as well as reducing the required fermentation volume. The vast majority of the fiber is contained in the solids within the wet distiller's grain and therefore the final product yield is virtually unchanged. The thin stillage from this process would either be used as recycle in the facility 10, or evaporated to form syrup. This syrup could either be sold separately, or dried in with the DDGS from the whole stillage fermentation process.

The whole stillage is then subjected to a pre-treatment process as depicted in block 204 of FIG. 2. In one embodiment, the pre-treatment process may be implemented with the equipment 50 generally illustrated in FIG. 3 and shown in more detail in FIG. 4. Referring to FIG. 4, the whole stillage is first transferred to a surge tank 52 or other vessel. Sulfuric acid or another acid is then added to the surge tank 52 to decrease the pH level of the whole stillage to promote dilute acid hydrolysis. Sufficient acid is supplied to decrease the pH of the whole stillage to 1.0 to 4.5 and preferably to 1.8. Some evidence suggests that lower pH values aid in oil recovery.

The pre-treatment portion of the process 200 continues by heating and pressurizing the whole stillage mixture. In one embodiment, the heating is performed in a hydro-heater 54 shown in FIG. 4 where high pressure steam is injected into the mixture to increase its temperature to 215° F. to 260° F., with the best results at 260° F. Higher temperatures up to 300° F. may be even more beneficial, but temperatures above 260° F. may be difficult to achieve economically. Heating by steam injection is beneficial because it results in cavitation of the mixture which further disrupts the structure of the fiber in the whole stillage which aids in subsequent processing of the whole stillage.

During the heating process, the whole stillage is also pressurized in the hydro-heater 54, a cook tube 56, or other vessel to a pressure in excess of the vapor pressure to prevent the mixture from boiling. The heated mixture is then held at the elevated temperature and pressure for 2-20 minutes. Applicant has discovered that retention times beyond 20 minutes don't provide substantial additional benefits.

Another method of heating the whole stillage is to use a heat exchanger where the steam, or other heating medium, does not come in contact with the whole stillage. This heating method produces very similar results to steam injection, but seems to require more residence time and is difficult to perform without fouling of the heat exchanger. This heating method also does not result in any cavitation of the whole stillage.

The pre-treatment portion of the process 200 continues by transferring the whole stillage mixture to a flash tank 58 where its pressure is rapidly dropped, causing the mixture to boil and flash off steam. This rapid boiling causes further rupturing of the fiber structure of the whole stillage to further expose the cellulose and hemicellulose of the whole stillage. The steam from the flash tank 58 may be captured in a flash condenser 60 and used as make-up water in the slurry tanks or elsewhere in the ethanol production facility 10 as depicted in FIG. 4.

Afterward, the whole stillage is cooled in one or more heat exchanges 62 to a temperature appropriate for the subsequent enzymatic hydrolysis process. Pentose sugars, such as xylose, may be produced from the hemicellulose by this portion of the method. Generally 75 to 100% of the final hemicellulose breakdown is achieved during the pre-treatment portion of the process 200 process. The enzymatic process that follows releases a bit more sugars from the hemicellulose.

The mixture is then subjected to an enzymatic hydrolysis process as depicted in block 212 of FIG. 2. In one embodiment, the enzymatic hydrolysis process may be implemented with the equipment 64 shown generally in FIG. 3 and shown in more detail in FIG. 4. The enzymatic hydrolysis primarily converts the cellulose portions of the fiber to usable sugars but also converts some of the hemicellulose to sugars. The whole stillage is first transferred to one or more tanks 66 shown in FIG. 4 where enzymes are added. Ammonia may also be added to increase the pH to a level conducive to the activity of the enzymes. In one embodiment, the whole stillage is held at a temp of 150° F.-160° F., with a preferred temp of 158° F. and a pH level of approximately 4.5. The whole stillage is then cooled in one or more heat exchangers 68 and, if necessary, pH corrected to a level of 4.8 to avoid denaturing the enzymes. Hexose sugars, such as glucose, may be produced from the cellulose by the enzymatic hydrolysis.

Depending on the nature of the enzyme used, the enzymatic hydrolysis can either be carried out during the fermentation steps described below where the temperature is held at a point that is conducive to fermentation, or as a separate step as described above in a separate tank where the temperature is held higher so the activity level of the enzymes is greater. The choice of a separate step or a simultaneous enzymatic and fermentation step depends on the activity of the enzymes used and on viscosity requirements. The whole stillage can become very viscous during the pretreatment steps, especially when cooled to fermentation temperature. It may therefore be necessary to cool the whole stillage to an intermediate temperature where the viscosity is lower and then add enzymes to breakdown the mixture further. The whole stillage can then be cooled to fermentation temperatures without excessive viscosity issues.

Different enzymes may be used to hydrolyze the hemicellulose and cellulose portions of the fiber. Hemicellulose composition varies from one fiber source to another, but all contain a variety of sugars with xylose generally being the most abundant. In corn fiber, xylose and arabinose are present in the highest concentrations. Mannose, glucose and other sugars are also present, but to a much smaller degree.

Hemicellulose can be broken down with enzymes that are currently commercially available, and by combining appropriate chemical and physical pretreatment methods the hydrolysis is quite effective. The enzymes used to hydrolyze hemicellulose are somewhat generically termed 'xylanases.' Xylanases contain several different enzymes that hydrolyze specific bonds in hemicellulose, but due to the fact that hemicellulose contains varying amounts of each of the sugars, varying amounts of each of the activities is required for an optimized hydrolyzation of all of the components. Xylanases are generally most effective at temperatures in the range of 155° F. to 185° F., with reduced activity at fermentation temperatures of 90° F. to 95° F.

Cellulose is more difficult to convert to sugars because of its crystalline structure. The glucose is linked to form chains, with cross linking between the chains. This cross linking of the chains creates much of the difficulty in hydrolyzing cellulose; in effect it creates a crystal structure with a relatively small surface area to volume ratio. The most effective way of hydrolyzing cellulose is to pretreat it as described above to rupture the fiber structure thereby creating more surface area. The cellulases are then introduced to continue the breakdown of the cellulose to glucose.

The enzymatic hydrolysis of the pretreated cellulose is usually accomplished in three steps. The first step is to cleave long chains of glucose from the cellulose using a whole cellulase, which randomly hydrolyzes links in the cellulose. Since this action is random in its attack it can create anything from a single glucose unit to a chain that is few thousand glucose units long. This is generally the cheapest portion of a cellulase formulation, but since it is random it does not produce free glucose units at a reliable rate. It does however create more chains for the next enzymes to act upon.

The second step is carried out by cellobiohydrolase. This enzyme hydrolyzes two units of glucose, termed cellobiose, from the end of a cellulose chain. Since this is not a random attack the rate of production of cellobiose is reliable.

The third enzyme used is beta-glucosidase. This enzyme acts on the end of a cellulose chain to hydrolyze single units of glucose. The chain can be of any length from two units to thousands of units long.

The best way to cost effectively hydrolyze cellulose is to balance the use of each one of these enzymes. For the cellobiohydrolase and beta-glucosidase to be effective they need ends to work on. The production of more ends is the job of the whole cellulase.

To further complicate matters, the temperature optimum for each of these enzymes is slightly different. The whole cellulase generally operates best at temperatures from 150° F. to 185° F., while beta-glucosidase operates in temperatures below 130° F., and is denatured at the optimum temperatures of the whole cellulase.

In light of this, it can be most cost effective to perform the above described pretreatment steps at a temperature near 160° F. and the add the cellulase alone in the enzymatic hydrolysis step. This can reduce the viscosity of the fluid and provide more ends for the cellobiohydrolase and beta-glucosidase to work on in fermentation. This step can also utilize the whole cellulase working in tandem with the xylanase, which is usually a higher temperature enzyme.

If viscosity is not an issue, it can be more cost effective to perform all of the enzymatic hydrolysis in fermentation rather than in a separate step. This provides a less capital intensive up-front investment. Additionally, many of the most cost effective enzymes available today contain all three of these enzyme activities in one mixture. Currently the decision on using an enzymatic pretreatment is solely based on viscosity.

The whole stillage is next fermented as depicted by block 208 in FIG. 2 and equipment 70 in FIG. 3. The fermentation of the mixed sugars produced in the pre-treatment and enzymatic hydrolysis steps described above requires an organism different than the yeast used in the fermentation step of the main ethanol production facility 10. *Saccharomyces cerevisiae* is only able to ferment hexose sugars, and therefore cannot use the pentose sugars unlocked from the hemicelluloses. Another yeast or bacteria is needed to perform this step.

*Saccharomyces cerevisiae* can be used, but two outcomes occur. Either an infectious organism begins to consume the pentose and some of the hexose sugars, or no infection occurs and the pentose sugars remain in solution. In the first case, the final acid detergent fiber content of the whole stillage byproduct of the process 200 is reduced and protein content is increased, with a slight change in amino acid profile. In the second case, the acid detergent fiber levels of the whole stillage byproduct remain higher with a resultant reduction in the percentage of protein.

The two front runners for the mixed sugar fermentation are both yeasts. The two strains are very similar in most respects. The first strain, *Pichia Stipitis*, is the most likely candidate because it is readily available. *Candida Shehatae* is the second candidate, but it is similar in most respects to *Pichia Stipitis* except that it is less readily available.

These yeasts are able to ferment both the glucose and the xylose contained in the mixture. This is a trait which greatly enhances the process 200. Fermentation times appear rather long, with 70 to 100 hours as the range found in other publications. The upper final ethanol concentrations these yeasts can survive is around 3.5 to 5 wt %. This is not an issue as the whole stillage is dilute enough to only produce final ethanol concentrations of around 1.5 to 3 wt %. If either of these yeasts are used, the entire fermentation would be carried out by the *Pichia Stipitis* or *Candida Shehatae*. No co-fermentation with *Saccharomyces cerevisiae* would be required, but could be done.

The fermentation step of the process 200 enhances the nutrient value of the final byproduct of the process 200. The yeasts are rich in proteins and are used to enhance the protein levels and the amino acid profiles of the whole stillage byproduct of the process 200. It would therefore be conceivable that someone could want to produce only yeast during this process, without the production of additional ethanol. This could remove the requirement for the distillation 72 and enhance the feed produced from the whole stillage byproduct even further.

A total fermentation time of ~20 hours can be used to ferment ~80% of the available sugars. This gives reasonable results to the process 200. However, additional time allows more fiber to be hydrolyzed and fermented, improving yields and feed composition. Generally, by 90 to 100 hours, the fermentation is nearly halted due to exhaustion of the feedstock. If fermentation is further extended beyond this point, the yeast will go through autolysis and begin to consume their own structural carbohydrates. This step increases the protein levels of the whole stillage byproduct but does little to nothing for final ethanol yields. A $CO_2$ containing gas is also produced in the fermentation step, which is not shown on FIG. 2.

After fermentation, whole stillage is distilled and separated as depicted by block 210 in FIG. 2 to remove ethanol from the whole stillage. The distillation may be performed in one or more distillation columns 72 depicted in FIG. 3. The distillation portion of the process 200 is similar to the distillation that occurs in the distillation columns 24 of the main ethanol production facility 10. The ethanol or alcohol exits the top of the columns 72 and is transferred to one or more rectifiers to remove moisture from the alcohol. The alcohol may also be passed to one or more molecular sieves to remove even more moisture. The final alcohol is then transferred to one or more ethanol holding tanks where it may be denatured before use as a fuel or fuel additive. The alcohol from the distillation columns 72 may be transferred to the rectifiers 26 and sieves 28 of the main ethanol production facility 10 where it is co-mingled with the ethanol from the distillation columns 24 or it may be purified by its own dedicated rectifiers and sieves.

The whole stillage that remains in the distillation columns 72 after the alcohol has been removed falls to the bottom of the distillation columns and is then transferred to one or more whole stillage holding tanks 74. The whole stillage at this point is similar to the whole stillage obtained at the beginning of the process 200 except that it has less solids and higher protein. The whole stillage may then be passed through one or more centrifuges 76 which separate the whole stillage into a stream of thin stillage and a stream of wet distillers grain. The thin stillage may be held in one or more tanks 78 and is typically returned to the slurry tanks 18 or some other part of the ethanol production facility 10 that requires water. Some or all of the thin stillage may also be transferred to one or more evaporators 80 to produce evaporated thin stillage, which is commonly referred to as "syrup". The syrup may be held in one or more tanks 82 and be used as an animal feed additive.

The wet distillers grain, which is often referred to as "wetcake", may be held in storage facilities 84, 86 and also sold as a livestock feed. Some of the wet distillers grain may be passed through one or more dryers 88 to remove liquid therefrom to produce dried distillers grain, which may be stored in one or more tanks 90 and used as dry livestock feed. The syrup from the tanks 82 may also be dehydrated in the dryers 88 forming dried distillers grain with solubles (DDGS).

The process 200 and systems described above provide numerous benefits. For example, the process 200 recovers additional ethanol from the whole stillage byproduct of the primary ethanol production facility 10, thus increasing the ethanol yield of the facility. Moreover, the process 200 also improves the quality of the final whole stillage byproducts. The dried distillers grain produced by the main ethanol production facility 10 has a high fiber content that is difficult for monogastrics to digest. The process 200 of the present invention uses that fiber as a carbohydrate that is metabolized by the fermentation step. During the initial stages of fermentation, the added yeast goes through a growth phase where the carbohydrates and available nitrogen are used to produce more yeast cells. The yeast are high in protein content and also produce essential amino acids. The reduction of fiber and increase of protein content produces a feed that is more digestable for monogastrics, and therefore much higher in value.

A conventional corn to ethanol process produces the following from one bushel of corn:

| Product | Yield | |
|---|---|---|
| Ethanol | 2.75 | Gallons per Bushel |
| DDGS | 16.4 | Pounds per Bushel |
| Corn Oil | 0.75 | Pounds per Bushel |

In contrast, an embodiment of the process 200 of the present invention produces the following from one bushel of corn:

| Product | Yield | |
|---|---|---|
| Ethanol | 3.02 | Gallons per Bushel |
| DDGS | 11.3 | Pounds per Bushel |
| Corn Oil | 1.05 | Pounds per Bushel |

Moreover, the process 200 improves the nutrient content of the final DDGS byproduct as follows:

| Type | Protein | Fat | Crude Fiber |
|---|---|---|---|
| Prior Art | 30% | 10% | 7% |
| Process 200 | 40% | 3% | 2% |

Embodiments of the invention may also be used to ferment whole stillage to other products. The sugars produced through the process 200 are relatively low in concentration as compared to traditional starch fermentations. This low concentration of fermentable sugars translates into low final concentrations of products. This allows fermentations with products that are toxic to the fermentation organism to be carried with low residual sugars.

One example of such a fermentation would be acetone, butanol, ethanol (ABE) fermentation. In this fermentation, butanol is toxic to the host organism at concentrations around 2%. If whole stillage is not concentrated prior to the fermentation, sugar concentrations of 3 to 4 wt % are expected. This would translate to final butanol concentrations of less than 2%. While ABE fermentation is used as the example many other types of fermentations would be well suited to this process.

The process 200 also improves corn oil recovery by breaking down the fiber and fermenting the fiber in the fat rich germ portion of the kernel. In prior art processes, the oil tends to become trapped within the fiber matrix of the germ, making it difficult to remove. Most reports of oil recovery in corn to ethanol plants with oil removal report yields of 15 to 35% of the total oil. By breaking down the fiber this number can increase to nearly 100% of total oil.

Important aspects of the present invention are depicted in FIGS. 5-10 and described below. These aspects of the invention provide methods/processes and systems for more effectively integrating traditional ethanol production facilities, such as those shown in FIG. 1, with cellulosic ethanol production facilities, such as those shown in FIGS. 3 and 4, to reduce overall energy use and produce ethanol with lower carbon intensity scores.

As mentioned above, biofuels, such as conventional corn ethanol, have relatively low CI scores because the CO2 emitted from vehicles during biofuel combustion is considered carbon neutral. But conventional corn ethanol production still has substantial direct and indirect GHG emissions. Lower GHG emissions associated with corn ethanol plants have reduced the CI scores of conventional ethanol from ~99 in 1990 to 50's and 60's in 2020, as shown in bars #1 and #2 in FIG. 5. This demonstrates that conventional corn ethanol can have lower CI scores than fossil fuel based gasoline, which has a CI of ~95.

Figure 5:
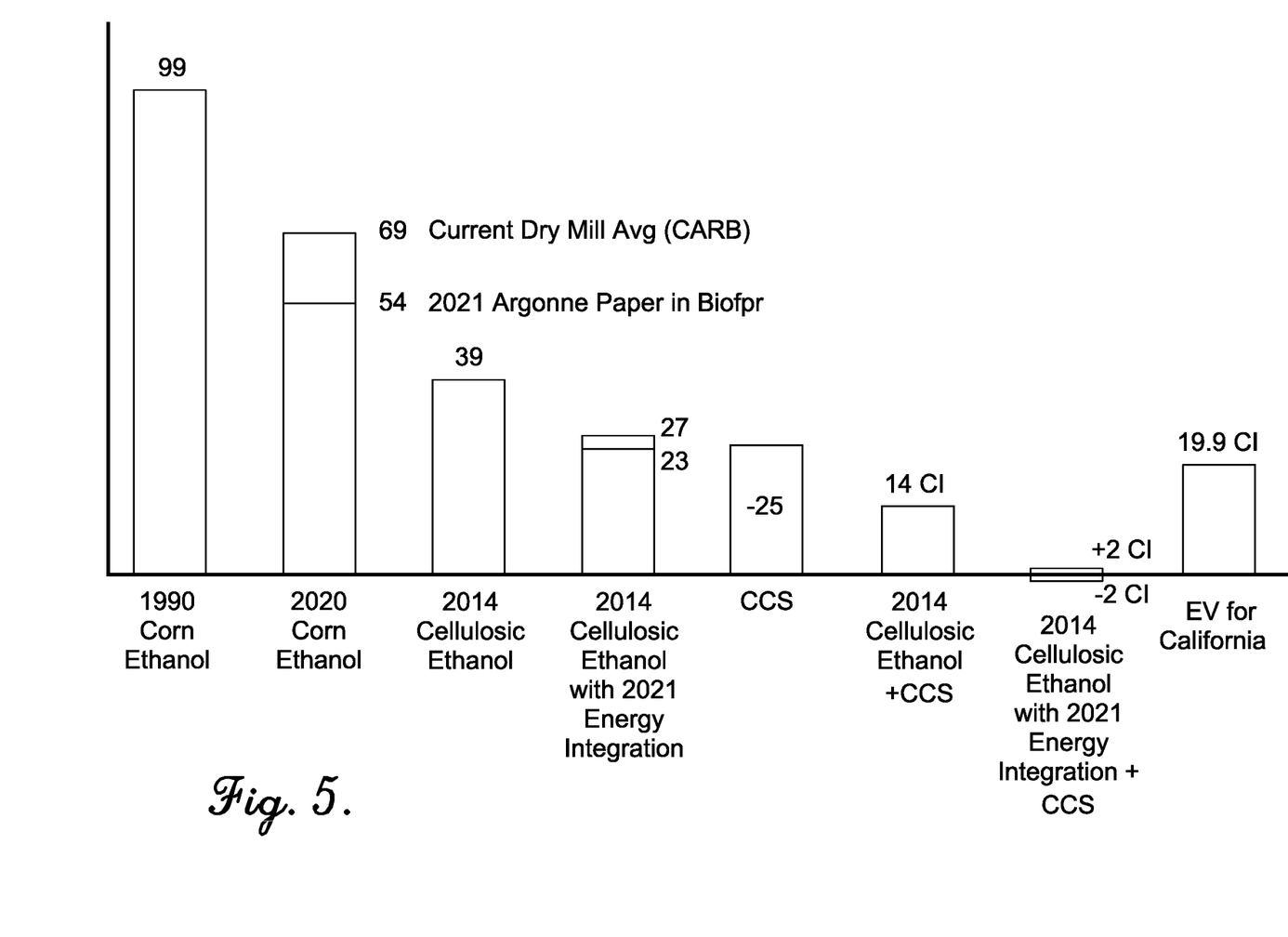
FIG. 5 is a graph showing the carbon intensity (CI) scores of ethanol made in accordance with several different methods as compared to the carbon intensity score of a fully electric vehicle charged with electricity generated mostly from renewable energy sources.

Because cellulosic ethanol is created from corn residuals or other byproducts of an existing ethanol production facility, and because these byproducts are classified as agriculture waste with zero CI, cellulosic ethanol has a much lower CI of 39, as shown in bar #3 in FIG. 5. However, as mentioned above, cellulosic ethanol production equipment is energy intensive, thus limiting its ability to lower CI levels further.

The present invention produces "ultra-low carbon intensity" ethanol, defined as ethanol with an ultra-low CI score, to compete with, or even exceed, the toughest benchmark of fully Electrical Vehicle (EV) in California. Such ultra-low carbon intensity ethanol can be produced via unique combinations of processes and systems from byproducts of an ethanol production facility.

Figure 6:
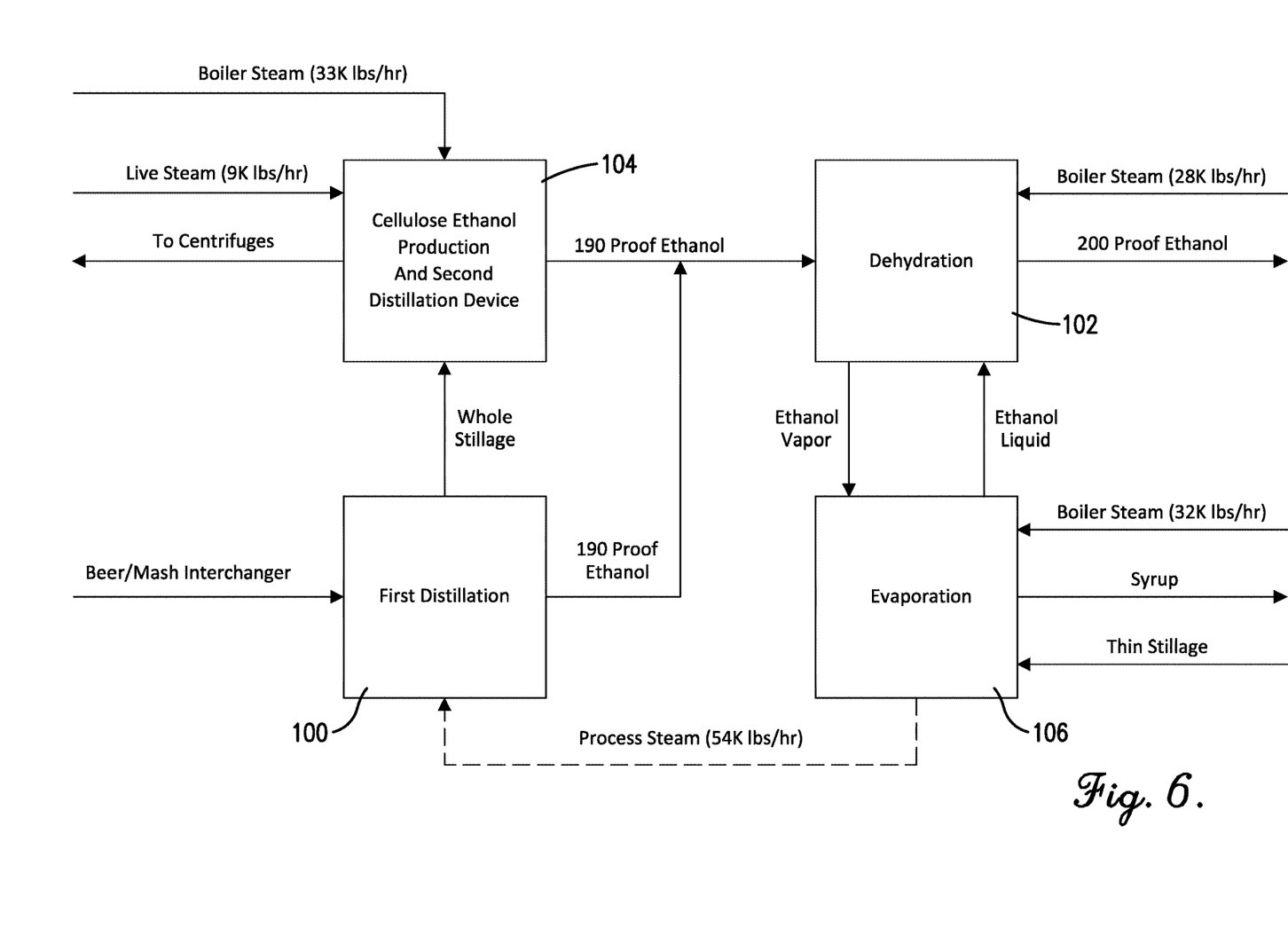
FIG. 6 is a block diagram that generally shows the flow of materials between a traditional ethanol production facility and cellulosic ethanol production equipment.

FIG. 6 generally shows the flow of materials between components of a traditional ethanol production facility and cellulosic ethanol production equipment. The traditional ethanol production facility has, among many other components, a first distillation device 100, which may be one or more of the distillation columns 24 shown in FIG. 1 or equivalent devices. The first distillation device 100, often referred to a "beer stripper", receives a "beer" mixture of alcohol, solids, and liquids from fermenting equipment and separates the alcohol from the solids and liquids. The alcohol, labeled as "190 Proof Ethanol" in FIG. 6, is then sent to dehydration equipment 102 to remove moisture from the alcohol. The dehydration equipment may be the rectifiers 26 and sieves 28 shown in FIG. 1 or equivalent devices. The traditional ethanol production facility also includes an evaporation device 106 and other components such as those shown in FIG. 1.

The first distillation device 100 delivers the separated solids and liquids, commonly called "whole stillage", to a second distillation device 104, which may be the distillation column 72 shown in FIG. 3 or an equivalent device. The whole stillage is subjected to other pre-treatment steps described in more detail above. The second distillation device 104 and associated equipment show in FIGS. 3 and 4 take whole stillage as feedstock and produces additional cellulosic ethanol via pre-treatment, fermentation, and separation. The ethanol, labeled as "190 Proof Ethanol" in FIG. 6, is then sent to the dehydration equipment 102 to remove moisture from the alcohol. The solid and liquid residuals from the second distillation device 104, or wet stillage, is sent to centrifuges, such as the centrifuge 76 shown in FIG.

3, for additional product separation. The cellulosic ethanol equipment, including the second distillation device 104, is generally just an "add-on" to the traditional ethanol production facility and requires substantial additional steam to run the second distillation device and other components. This process develops ethanol with a CI score of 39 as shown in the third bar of FIG. 5.

Figure 7:
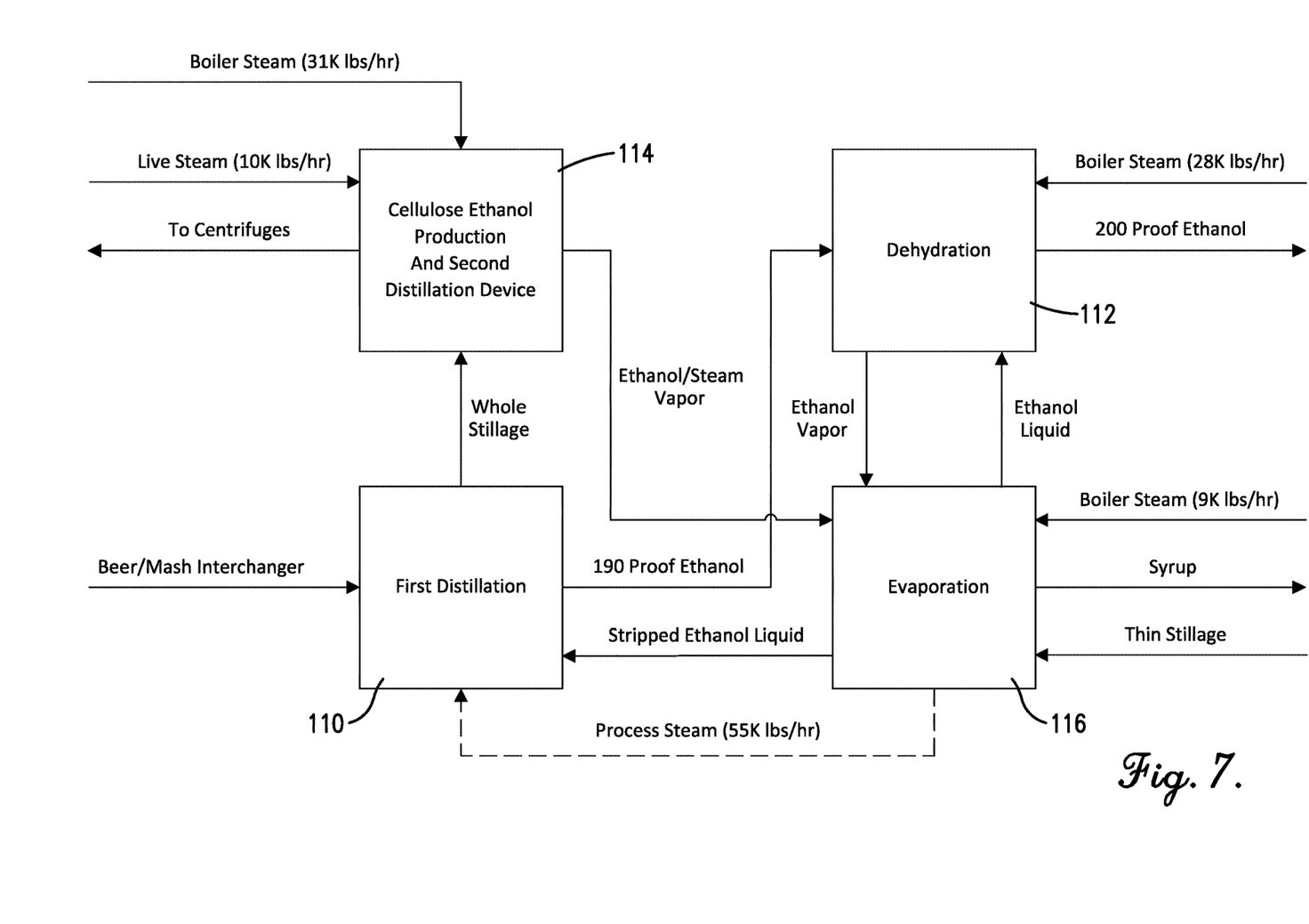
FIG. 7 is a block diagram that shows the flow of materials between the ethanol production facility and cellulosic ethanol equipment of FIG. 6 in ways that more effectively integrates facility and the equipment to reduce overall energy use and to produce ethanol with lower carbon intensity scores.

FIG. 7 shows the flow of materials between an ethanol production facility and cellulosic ethanol equipment in ways that more effectively integrates the equipment to reduce overall energy use and to produce ethanol with lower carbon intensity scores. Instead of simply adding the cellulosic ethanol production equipment to the existing ethanol plant, FIG. 7 shows processes and systems of energy integration and optimization between the two ethanol production facilities.

The traditional ethanol production facility has a first distillation device 110, which may be one or more of the distillation columns 24 shown in FIG. 1 or equivalent devices. The first distillation device 110 receives a "beer" mixture of alcohol, solids, and liquids from fermenting equipment and separates the alcohol from the solids and liquids. The alcohol, labeled as "190 Proof Ethanol" in FIG. 7, is then sent to dehydration equipment 112 to remove moisture from the alcohol. The dehydration equipment may be the rectifiers 26 and sieves 28 shown in FIG. 1 or equivalent devices. The whole stillage is delivered to a second distillation device 114, which may be the distillation column 72 shown in FIG. 3 or an equivalent device. The whole stillage is subjected to other pre-treatment steps described in more detail above.

The second distillation device 114 and associated equipment shown in FIGS. 3 and 4 produce additional cellulosic ethanol from the whole stillage via pretreatment and fermentation. As shown in FIG. 7, the second distillation device takes the same whole stillage feedstock from the first distillation device; however, it does not produce additional cellulosic ethanol as 190 proof ethanol, but instead as ethanol/steam mixed vapor. This ethanol/steam vapor is sent to evaporation equipment 116 to be used as a part of the heat source for the evaporation processes and systems. The evaporation equipment 116, which may include the evaporators 38 and/or the evaporators 80 described above, condenses the ethanol/steam mixed vapor to create stripped ethanol liquid, which is routed to the first distillation device 110 to produce additional 190 proof ethanol. The steam produced by evaporation equipment 116 is routed to the first distillation device 110, shown as the dotted line between 116 and 110 in FIG. 7, to be used as a part of the heat source for the first distillation device 110. The wet stillage from the second distillation device 114, is sent to centrifuges, such as the centrifuge 76 shown in FIG. 3, for additional product separation.

As shown in FIG. 7, the total steam usage of the cellulosic ethanol production equipment and the components of the traditional ethanol production facility is significantly reduced, compared to FIG. 6. The improves the CI score of the resultant ethanol to 23-27 as shown by bar #4 in FIG. 5.

Figure 8:
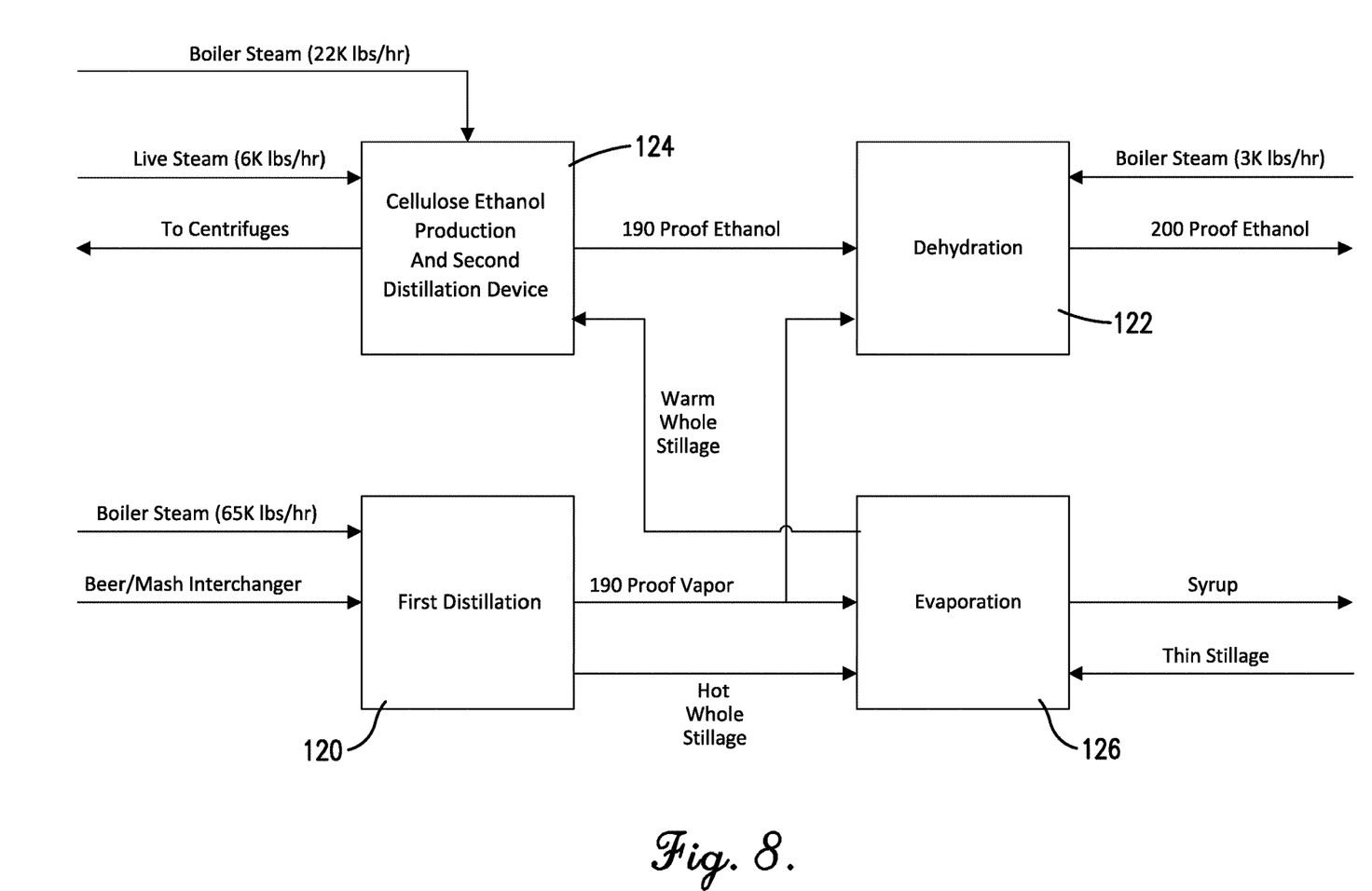
FIG. 8 is a block diagram that generally shows the flow of materials between another type of traditional ethanol production facility and cellulosic ethanol production equipment.

FIG. 8 shows the flow of materials between another type of traditional ethanol production facility and cellulosic ethanol equipment. In this example, the traditional ethanol plant has a first distillation device 120 that utilizes a pressurized distillation process (e.g., Delta T). The first distillation device 120 receives a "beer" mixture of alcohol, solids, and liquids from fermenting equipment and separates the alcohol from the solids and liquids. The alcohol, labeled as "190 Proof Ethanol" in FIG. 8, is then sent to dehydration equipment 122 and/or evaporation equipment 126 to remove moisture from the alcohol. The dehydration equipment may be similar to the rectifiers 26 and sieves 28 shown in FIG. 1 or equivalent devices.

The first distillation device 120 also delivers heated whole stillage to the evaporation equipment 16, which then passes warm whole stillage to a second distillation device 124. Because of higher pressure and high temperature of the pressurized distillation in this type of corn ethanol plant, the hot whole stillage is directed to the evaporation system as a heat source.

The second distillation device 124, along with other equipment described above, produces additional ethanol from the whole stillage via pretreatment and fermentation. The ethanol, labeled as "190 Proof Ethanol" in FIG. 8, is then sent to the dehydration equipment 122 to remove moisture from the alcohol. The wet stillage from the second distillation device, is sent to centrifuges, such as the centrifuge 76 shown in FIG. 3, for additional product separation.

Figure 9:
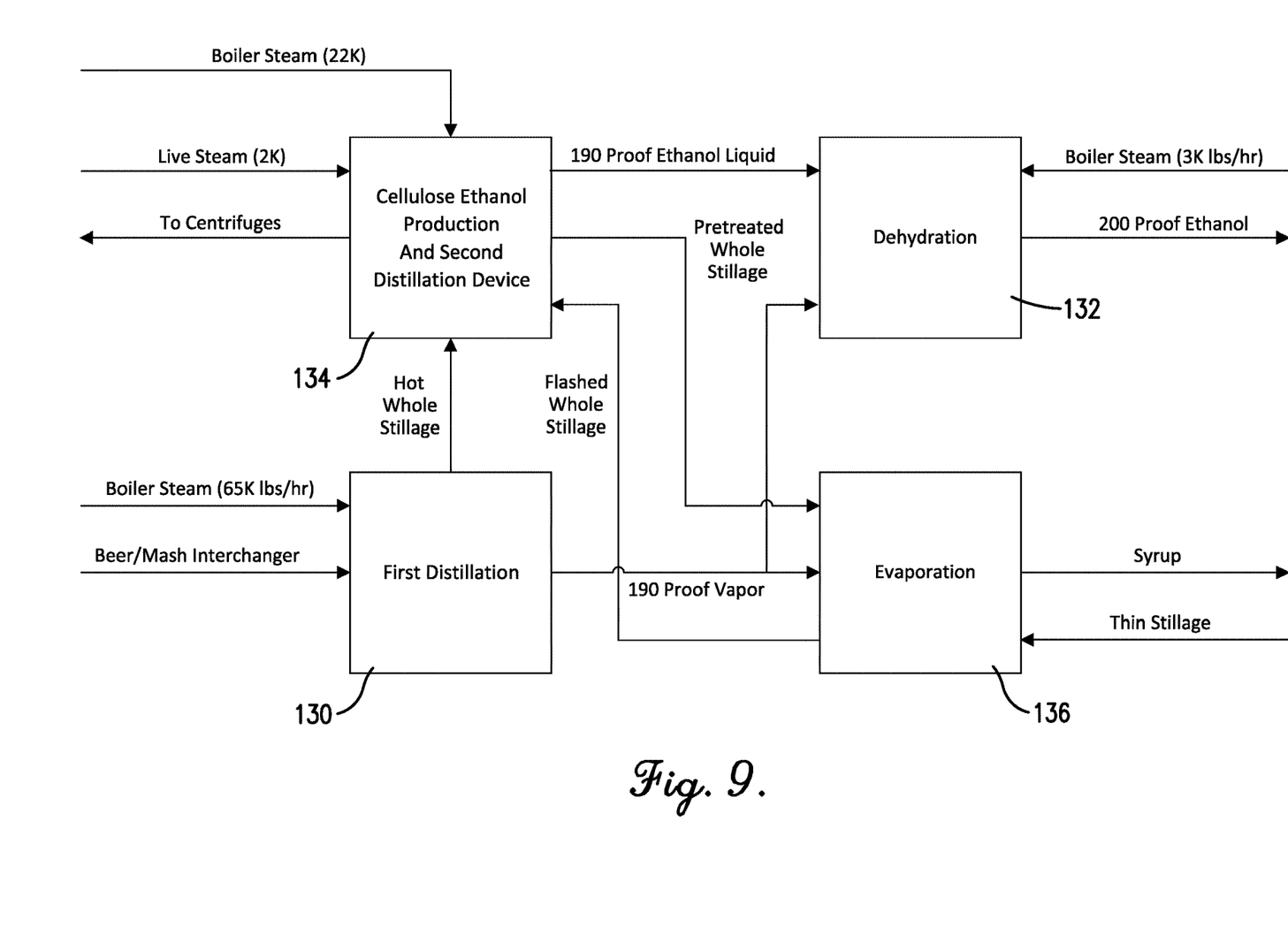
FIG. 9 is a block diagram that shows the flow of materials between the ethanol production facility and cellulosic ethanol equipment of FIG. 8 in ways that more effectively integrates the facility and equipment to reduce overall energy use and to produce ethanol with lower carbon intensity scores.

FIG. 9 shows the flow of materials between the ethanol production facility and cellulosic ethanol equipment of FIG. 8 in ways that more effectively integrates the equipment to reduce overall energy use and to produce lower carbon intensity scores of the ethanol. This aspect of the invention recognizes that the hot whole stillage from the first distillation device 130, which has a temperature of 240F to 250F, is close to the energy requirements of the second distillation device 134 and its associated cellulosic ethanol production equipment. Thus, the first distillation device 130 feeds the hot whole stillage directly to the second distillation device 134 and its associated cellulosic ethanol production equipment. The second distillation device 134 then delivers pre-treated whole stillage to the evaporation system 136 to partially supply the energy requirements of the evaporator system.

The total live steam usage for the cellulosic ethanol production equipment is reduced from 6K lb/hr to 2K lb/hr due to this energy integration which saves energy and hence further reduces the ethanol's CI score.

Figure 10:
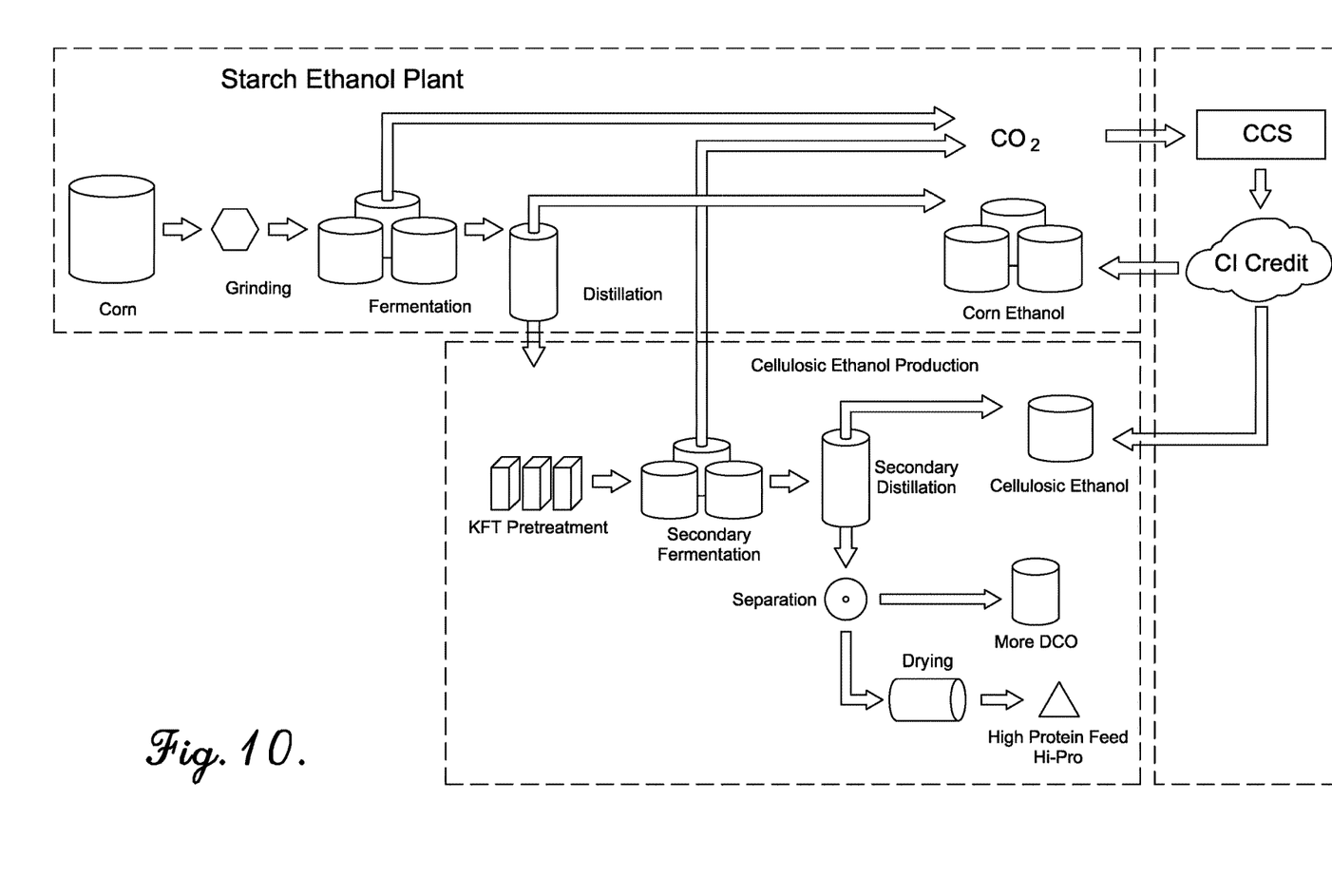
FIG. 10 is a block diagram that shows the integration of an ethanol production facility, cellulosic ethanol equipment, and carbon capture and sequestration (CCS) equipment in ways that more effectively integrates the equipment to reduce overall energy use and to produce ethanol with lower carbon intensity scores.

FIG. 10 illustrates processes and systems for integrating an ethanol production facility, cellulosic ethanol production equipment, and carbon capture and sequestration (CCS) equipment in ways that produces even lower carbon intensity scores for ethanol. CCS is a process which includes systems for collecting $CO_2$ containing gas from the source, processing, compressing, transporting the $CO_2$ containing gas, and injecting the compressed gas into an underground storage site. Corn ethanol plants produce high purity $CO_2$ gas during fermentation process, which is highly suitable for CCS process. Recent studies showed that CCS's CI credit is about 25, as shown in bar #5 in FIG. 5. Cellulosic ethanol production also produces high purity $CO_2$ gas. As shown in FIG. 10, $CO_2$ containing gases from both a traditional ethanol plant and a cellulosic ethanol production facility are collected and sent to CCS for sequestration, which generates CI credit that is transferred to the ethanol products associated with the $CO_2$ gas. This results in ethanol with CI scores near zero as shown by bar #7 in FIG. 5.

The above-described systems and equipment, and equivalent systems and equipment, may implement methods/processes of producing ethanol from both the starch and fiber components of grains in a manner that reduces overall energy use and that produces ethanol with extremely low CI scores. One process comprises creating a first supply of ethanol from starch components of the grains with a first distillation device that requires energy of a first amount and an evaporator that requires energy of a second greater amount. The process further comprises creating a second supply of ethanol from fiber portions of the grains with a second distillation device that requires energy of a third yet even greater amount. To integrate more efficiently the two ethanal production steps, the process further comprises transferring at least some of the energy from the second distillation device to the evaporator to reduce energy requirements of the evaporator and transferring at least some of energy from the evaporator to the first distillation device to reduce energy requirements of the first distillation device.

In one embodiment, the energy required by the first distillation device is supplied by steam having a pressure between 7-9 psia; the energy required by the evaporator is supplied by steam having a pressure between 9-14 psia; and the energy required by the second distillation is supplied by steam having a pressure greater than 14 psia.

Another process comprises creating a first supply of ethanol from starch components of the grains and heated whole stillage from fiber portions of the grains with a first distillation device and then passing the heated whole stillage from the first distillation device to a second distillation device. The process further comprises creating with the second distillation device a second supply of ethanol and pre-treated whole stillage and passing the pre-treated whole stillage to an evaporator for drying. To integrate more efficiently the two ethanal production steps, the process further comprises using energy in the heated whole stillage to provide at least some of the energy requirements of the second distillation device and using energy in the pre-treated whole stillage to provide at least some of the energy requirement of the evaporator.

In one embodiment, the first distillation device employs a pressurized distillation process; the heated whole stillage has a temperature of 240-250 degrees F.; and the pre-treated whole stillage has a temperature of 180-240 degrees F.

Another process comprises milling grains into a grain powder; adding water and enzymes to the grain powder to create a grain mixture; fermenting the grain mixture to create a beer mixture; passing the beer mixture to a first distillation device; separating alcohol in the beer mixture from whole stillage with the first distillation device to create a first supply of ethanol; removing water from a waste portion of the whole stillage with an evaporator; heating the whole stillage to create pre-treated whole stillage; fermenting the pre-treated whole stillage to create a second beer mixture; passing the second beer mixture to a second distillation device; separating alcohol in the second beer mixture from whole stillage with the second distillation device to create a second supply of ethanol; passing waste heat from the second distillation device to the evaporator to reduce heating requirements of the evaporator; and passing waste heat from the evaporator to the first distillation device to reduce heating requirements of the first distillation device.

Additional Considerations

In this description, references to "one embodiment," "an embodiment," or "embodiments" mean that the feature or features being referred to are included in at least one embodiment of the technology. Separate references to "one embodiment," "an embodiment," or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments but is not necessarily included. Thus, the current technology can include a variety of combinations and/or integrations of the embodiments described herein.

Although the present application sets forth a detailed description of numerous different embodiments, the legal scope of the description is defined by the words of the claims set forth at the end of this patent and equivalents. The detailed description is to be construed as exemplary only and does not describe every possible embodiment since describing every possible embodiment would be impractical. Numerous alternative embodiments may be implemented, using either current technology or technology developed after the filing date of this patent, which would still fall within the scope of the claims.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus.

The patent claims at the end of this patent application are not intended to be construed under 35 U.S.C. § 112 (f) unless traditional means-plus-function language is expressly recited, such as "means for" or "step for" language being explicitly recited in the claim(s).

Although the invention has been described with reference to the embodiments illustrated in the attached drawing figures, it is noted that equivalents may be employed and substitutions made herein without departing from the scope of the invention as recited in the claims.

Having thus described various embodiments of the invention, what is claimed as new and desired to be protected by Letters Patent includes the following:

The invention claimed is:

1. A method of reducing energy usage while producing additional ethanol from an ethanol facility, the method comprising:
  a) producing a first product of ethanol from a first distillation device that operates at a first temperature and requires energy of a first amount and an evaporator that operates at a second temperature and requires energy of a second amount;
  b) producing a second additional product of ethanol from a second distillation device that receives whole stillage from the first distillation device and that operates at a third temperature and requires energy of a third amount;
  c) transferring at least part of the third amount of energy from the second distillation device to the evaporator to reduce at least part of the second amount of energy requirements for the evaporator; and d) transferring at least part of the second amount of energy from the evaporator to the first distillation device to reduce at least part of the first amount of energy requirements for the first distillation device.

2. The method as set forth in claim 1, wherein step (c) is at least partially implemented by delivering an ethanol/steam mixed vapor from the second distillation device to the evaporator whereby the evaporator uses heat from the ethanol/steam mixed vapor to provide at least some of its energy requirements.

3. The method as set forth in claim 1, wherein step (d) is at least partially implemented by delivering steam from the evaporator to the first distillation device.

4. The method as set forth in claim 1, wherein the energy required by the first distillation device is supplied by steam from the evaporator having a pressure between 7-9 psia.

5. The method as set forth in claim 1, wherein the energy required by the evaporator is supplied by ethanol/steam mixed vapor from the second distillation having a pressure between 9-14 psia.

6. The method as set forth in claim 1, wherein the energy required by the second distillation is supplied by steam having a pressure greater than 14 psia.

7. The method as set forth in claim 1, wherein the producing the first product of ethanol step uses fiber portions of grains as a feedstock.

8. The method as set forth in claim 7, wherein the fiber portions of the grains are corn kernels.

* * * * *